US008940940B2

(12) United States Patent  
Dehn et al.

(10) Patent No.: US 8,940,940 B2
(45) Date of Patent: Jan. 27, 2015

(54) PROCESS FOR PREPARING MACROCYCLIC KETONES

(71) Applicant: BASF SE, Ludwigshafen (DE)

(72) Inventors: Richard Dehn, Ludwigshafen (DE); Joaquim Henrique Teles, Waldsee (DE); Michael Limbach, Worms (DE); Stephan Deuerlein, Ludwigshafen (DE); Manuel Danz, Eppelheim (DE); Ralf Pelzer, Fürstenberg (DE); Daniel Schneider, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/916,082

(22) Filed: Jun. 12, 2013

(65) Prior Publication Data
US 2013/0338402 A1 Dec. 19, 2013

Related U.S. Application Data

(60) Provisional application No. 61/658,931, filed on Jun. 13, 2012.

(51) Int. Cl.
| C07C 45/68 | (2006.01) |
| C07C 49/547 | (2006.01) |
| A61K 31/12 | (2006.01) |
| C07C 45/67 | (2006.01) |
| C07C 49/527 | (2006.01) |

(52) U.S. Cl.
CPC .............. C07C 45/68 (2013.01); C07C 45/673 (2013.01); C07C 49/547 (2013.01); C07C 49/527 (2013.01); C07C 2101/18 (2013.01)
USPC ........... 568/343; 568/351; 568/375; 514/690; 512/27

(58) Field of Classification Search
CPC .... C07C 45/68; C07C 45/673; C07C 2101/18
USPC .............. 568/343, 351, 375; 512/27; 514/690
See application file for complete search history.

(56) References Cited

U.S. PATENT DOCUMENTS

| 3,450,732 | A | 6/1969 | Wilke et al. |
| 4,668,836 | A | 5/1987 | Eberle et al. |
| 4,885,397 | A | 12/1989 | Bueschken |
| 5,936,100 | A | 8/1999 | Fürstner et al. |
| 5,969,170 | A | 10/1999 | Grubbs et al. |
| 6,111,121 | A | 8/2000 | Grubbs et al. |
| 6,552,139 | B1 | 4/2003 | Herrmann et al. |
| 6,921,735 | B2 | 7/2005 | Hoveyda et al. |
| 8,410,293 | B2 | 4/2013 | Ebel et al. |
| 2003/0069460 | A1 | 4/2003 | Wohrle et al. |
| 2006/0281952 | A1 | 12/2006 | Teles et al. |
| 2007/0043180 | A1 | 2/2007 | Zhan |
| 2008/0255393 | A1 | 10/2008 | Teles et al. |
| 2008/0274032 | A1 | 11/2008 | Teles et al. |
| 2009/0318733 | A1 | 12/2009 | Pinkos et al. |
| 2010/0018389 | A1 | 1/2010 | Baumann et al. |
| 2010/0191018 | A1 | 7/2010 | Teles et al. |
| 2011/0003905 | A1 | 1/2011 | Buchmeiser et al. |
| 2011/0023538 | A1 | 2/2011 | Teles et al. |
| 2011/0023713 | A1 | 2/2011 | Rössler-Feigel et al. |
| 2011/0282068 | A1 | 11/2011 | Herrmann et al. |
| 2012/0088935 | A1 | 4/2012 | Schelper et al. |
| 2012/0142950 | A1 | 6/2012 | Teles et al. |
| 2012/0165588 | A1 | 6/2012 | Dehn et al. |
| 2012/0203013 | A1 | 8/2012 | Weyrauch et al. |
| 2012/0277101 | A1 | 11/2012 | Klingelhoefer et al. |
| 2013/0005641 | A1 | 1/2013 | Ebel et al. |
| 2013/0018205 | A1 | 1/2013 | Teles et al. |
| 2013/0053582 | A1 | 2/2013 | Malkowsky et al. |
| 2013/0072726 | A1 | 3/2013 | Schuch et al. |
| 2013/0144060 | A1 | 6/2013 | Mauduit et al. |
| 2013/0172616 | A1 | 7/2013 | Limbach et al. |

FOREIGN PATENT DOCUMENTS

| DE | 1283836 B | 11/1968 |
| DE | 10142032 A1 | 3/2003 |
| DE | 102004046167.8 | 9/2004 |
| EP | 0182333 A1 | 5/1986 |
| EP | 0322537 A2 | 7/1989 |
| EP | 1022282 A2 | 7/2000 |
| EP | 08153952.0 | 4/2008 |
| EP | 08153953.8 | 4/2008 |
| WO | WO-99/00396 A1 | 1/1999 |
| WO | WO-99/51344 A1 | 10/1999 |
| WO | WO-03/062253 A1 | 7/2003 |
| WO | WO-2005/030690 A2 | 4/2005 |
| WO | WO-2006/032502 A1 | 3/2006 |
| WO | WO-2007003135 A1 | 1/2007 |
| WO | WO-2007/060160 A2 | 5/2007 |
| WO | WO-2008/000754 A1 | 1/2008 |
| WO | WO-2008/065187 A1 | 6/2008 |
| WO | WO-2008/071632 A2 | 6/2008 |
| WO | WO-2009/097955 A1 | 8/2009 |
| WO | WO-2010/021740 A | 2/2010 |

(Continued)

OTHER PUBLICATIONS

Clark et al. Synthesis of a Molecular Charm Bracelet via Click Cyclization an Olefin Metathesis Clipping. Journal of the American Chemical Society, 2010, vol. 132, 3405-3412.*
U.S. Appl. No. 13/884,503.
U.S. Appl. No. 13/751,604.
U.S. Appl. No. 13/850,594.
U.S. Appl. No. 61/504,246.
U.S. Appl. No. 61/551,949.
U.S. Appl. No. 61/658,937.

(Continued)

Primary Examiner — Sikarl Witherspoon
(74) Attorney, Agent, or Firm — Drinker Biddle & Reath LLP

(57) ABSTRACT

The present invention relates to a process for preparing cyclic compounds having at least eight carbon atoms and at least one keto group, to the cyclic compounds obtained by this process and to the use thereof, in particular as fragrance or for providing a fragrance.

19 Claims, No Drawings

(56) References Cited

FOREIGN PATENT DOCUMENTS

| | | |
|---|---|---|
| WO | WO-2010/037550 A1 | 4/2010 |
| WO | WO-2010/086314 A1 | 8/2010 |
| WO | WO-2011/117571 A1 | 9/2011 |
| WO | WO-2012/045786 A1 | 4/2012 |
| WO | WO-2012/062771 A1 | 5/2012 |
| WO | WO-2012/076543 A1 | 6/2012 |
| WO | WO-2012/084673 A1 | 6/2012 |
| WO | WO-2012/107877 A1 | 8/2012 |
| WO | WO-2012/146623 A1 | 11/2012 |
| WO | PCT/EP2013/051034 | 1/2013 |
| WO | WO-2013/000842 A1 | 1/2013 |
| WO | WO-2013/000846 A1 | 1/2013 |
| WO | WO-2013/004579 A2 | 1/2013 |
| WO | WO-2013/007561 | 1/2013 |
| WO | WO-2013/026737 A2 | 2/2013 |
| WO | PCT/EP2013/056201 | 3/2013 |
| WO | WO-2013/037737 A1 | 3/2013 |
| WO | PCT/EP2013/062077 | 6/2013 |
| WO | WO-2013/098772 | 7/2013 |

OTHER PUBLICATIONS

Story, P., et. al., "Modern Methods for the Synthesis of Macrocyclic Compounds", Adv. Org. Chem., vol. 8, (1972), pp. 67-95.

Mookherjee, B., et. al., "Synthesis of Racemic Muscone and Cyclopentadecanone (Exaltone) from 1,9-Cyclohexadecadiene", J. Org. Chem., vol. 36, No. 22, (1971), pp. 3266-3270.

International Search Report for PCT/EP2013/062077, dated Sep. 6, 2013.

Williams, A., et al., "The Synthesis of Macrocyclic Musks", Synthesis, No. 10, (1999), pp. 1707-1723.

* cited by examiner

PROCESS FOR PREPARING MACROCYCLIC KETONES

RELATED APPLICATIONS

This application claims benefit (under 35 USC 119(e)) of U.S. Provisional Application Ser. No. 61/658,931, filed Jun. 13, 2012, which is incorporated herein by reference in its entirety.

BACKGROUND OF THE INVENTION

The present invention relates to a process for preparing cyclic compounds having at least eight carbon atoms and at least one keto group, to the cyclic compounds obtained by this process and to the use thereof, in particular as fragrance or for providing a fragrance.

There is a need for effective processes for preparing cyclic compounds based on medium and specifically based on large rings which have at least one keto group. Medium rings generally have 8 to 11 carbon atoms, above 12 carbon atoms one talks of large rings, and compounds based on large rings are also referred to as macrocyclic compounds. Macrocyclic ketones, lactones and epoxides as well as further functionalized macrocycles are aroma chemicals valued in the fragrance industry. Important representatives are e.g. muscone (1), (E/Z)-8-cyclohexadecenone (2), cyclohexadecanone (3) or 9-hexadecen-16-olide (4).

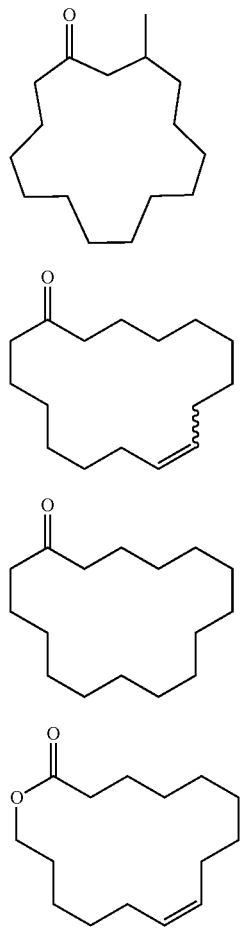

The known processes for preparing cyclic ketones are generally associated with considerable synthetic expenditure.

Thus, A. S. Williams gives, in Synthesis 1999, 10, 1707-1723, an overview of the synthesis of macrocyclic musk compounds. For example, the preparation of muscone (1) takes place according to this in a multistage synthesis starting from cyclododecanone by ring expansion.

DE 101 42 032 A1 describes the preparation of cycloalkadienes from cycloalkamonoenes, cyclopolyenes, acyclic polyenes or mixtures thereof by metathesis reaction in the presence of an $Re_2O_7/\gamma\text{-}Al_2O_3$ catalyst. Specifically, the preparation of 1,9-cyclohexadecadiene from cyclooctene is described.

B. D. Mookherjee et al. described in J. Org. Chem. 36, 22 (1971), 3266-3270 the synthesis of racemic muscone and cyclopentadecanone (exalton) starting from 1,9-cyclohexadecadiene. The synthesis comprises a complex reaction sequence which comprises inter alia an epoxidation step and a rearrangement step.

EP 0322537 A2 describes a process for preparing cyclic ketones by isomerization of epoxides in a polar solvent in the presence of alkali metal or alkaline earth metal halides.

U.S. Pat. No. 5,936,100 describes the synthesis of functionalized macrocycles by ring-closure metathesis. Thus, for example, the synthesis of 9-hexadecen-16-olide (D) takes place by ring-closure metathesis of 10-undecenylic acid 5-hexenyl ester. However, the starting material diene is only poorly available on an industrial scale.

Paul R. Story and P. Busch describe in "Modern methods for the synthesis of macrocyclic compounds", Adv. Org. Chem. 1972, 8, 67-95 diverse synthesis routes, inter alia by means of ring expansion, ring reduction, 1,2-cycloaddition, etc. The so-called "Story synthesis" comprises here the formation and destruction of corresponding peroxides, which is associated with correspondingly high synthetic and safety expenditure.

The known processes for preparing cyclic compounds having at least eight, specifically at least 12, ring carbon atoms are either multistage syntheses or start from starting materials that are only poorly available on an industrial scale.

Cyclododecanone is an important intermediate for preparing lauryl lactam, dodecanedicarboxylic acid and polyamides derived therefrom. To prepare cyclododecanone, 1,5,9-cyclododecatriene can be subjected to an oxidation, specifically an oxidation with $N_2O$, the main product obtained being cyclododeca-4,8-dienone, which is then subjected to a selective hydrogenation to give cyclododecanone. Processes of this type are described for example in WO 2005/030690, WO 2008/000754 and WO 2010/086314.

Surprisingly, it has now been found that, starting from cyclododeca-4,8-dienone, it is possible to prepare cyclic compounds having at least eight carbon atoms and at least one keto group simply and effectively by means of metathesis reaction. Here, specifically the preparation of a metathesis product which has a high fraction of macrocyclic ketones and diketones of ring sizes $C_{16}$, $C_{20}$, $C_{24}$ and higher homologues having in each case four additional carbon atoms is possible. This metathesis product is suitable, optionally after separation into fractions or essentially pure compounds, as fragrance or for providing a fragrance. Moreover, this process is particularly advantageous since cyclododeca-4,8-dienone is industrially available in large amounts as intermediate of the preparation of cyclododecanone. Furthermore, only one synthesis step is required in order to obtain a product which can have a large number of interesting compounds. Thus, the metathesis products obtainable by the process according to the invention or fractions or essentially pure compounds therefrom can also serve as valuable intermediates. They are suitable for further processing e.g. by hydrogenation, Baeyer-Villiger oxidation to give macrocyclic lactones, synthesis building blocks of diverse specialty chemicals and fragrances, etc.

SUMMARY OF THE INVENTION

The invention firstly provides a process for preparing at least one cyclic compound having a least eight carbon atoms and at least one keto group in which
a) a cyclododeca-4,8-dienone-containing starting material is provided, and
b) the starting material is subjected to an olefin metathesis reaction in the presence of a transition metal catalyst.

The invention further provides a composition which comprises at least one cyclic compound having at least eight carbon atoms and at least one keto group and which is available by the process described above and below.

The invention further provides the use of at least one cyclic compound which is obtainable by the process described above and below as fragrance or for providing a fragrance.

The invention further provides a cosmetic composition, a consumer good or utility item which comprises an organoleptically effective amount of at least one cyclic compound which is obtainable by the process described above and below as fragrance.

DESCRIPTION OF THE INVENTION

Step a)

In step a) of the process according to the invention, pure cyclododeca-4,8-dienone or an industrially available cyclododeca-4,8-dienone-containing mixture can be used as cyclododeca-4,8-dienone-containing starting material.

Preferably, to provide the cyclododeca-4,8-dienone-containing starting material in step a), a 1,5,9-cyclododecatriene-containing composition is used and subjected to an oxidation, giving an oxidation product which comprises cyclododeca-4,8-dienone.

1,5,9-Cyclododecatriene can generally be used in the form of any possible isomer, for example cis,trans,trans-1,5,9-cyclododecatriene, cis,cis,trans-1,5,9-cyclododecatriene, all-trans-1,5,9-cyclododecatriene or all-cis-1,5,9-cyclododecatriene. In step a) of the process according to the invention, it is also possible to use an isomer mixture which comprises at least two of the aforementioned isomers.

The 1,5,9-cyclododecatriene used in the process according to the invention can generally be obtained by all processes known to the person skilled in the art for its preparation. In a preferred embodiment, the 1,5,9-cyclododecatriene is prepared by trimerization of butadiene.

1,5,9-Cyclododecatriene can be prepared for example by trimerization of pure 1,3-butadiene, as is described, for example, in T. Schiffer, G. Oenbrink, "Cyclododecatriene, Cyclooctadiene, and 4-Vinylcyclohexene", in Ullmann's Encyclopedia of Industrial Chemistry, 6th Edition (2000), Electronic Release, Wiley VCH, pages 1 to 4. In the course of this process, for example in the case of the trimerization in the presence of Ziegler-catalysts cis,trans,trans-1,5,9-cyclododecatriene, cis,cis,trans-1,5,9-cyclododecatriene and all-trans-1,5,9-cyclododecatriene, as is described for example in H. Weber et al. "Zur Bildungsweise von cis,trans,trans-1,5,9-Cyclododecatrien mittels titanhaltiger Katalysatoren [The mode of formation of cis,trans,trans-1,5,9-cyclododecatriene by means of titanium-containing catalysts]" in Liebigs Ann. Chem. 681 (1965), pages 10 to 20 are produced. Cyclododecatriene can be prepared for example by trimerization of 1,3-butadiene using a titanium or nickel catalyst. This is described for example in DE 1283836.

A preferred titanium catalyst for the trimerization of butadiene is a titanium tetrachloride/ethylaluminum sesquichloride catalyst, as is described e.g. in H. Weber et al., Liebigs Ann. Chem. 681 (1965), pages 10 to 20.

A preferred nickel catalyst for the trimerization of butadiene is the bis-cyclooctadienylnickel/ethoxydiethylaluminum catalyst described in DE 1283836.

The butadiene used for the trimerization preferably has a degree of purity, determined by gas chromatography, of at least 99.5%. Particularly preferably, the 1,3-butadiene used comprises no 1,2-butadiene and no 2-butyne within the limits of detection accuracy.

The mixtures obtained during the trimerization of butadiene have preferably at least 95% by weight, particularly preferably at least 96% by weight, in particular at least 97% by weight of cis,trans,trans-1,5,9-cyclododecatriene.

In a preferred embodiment, the 1,5,9-cyclododecatriene-containing composition is subjected to an oxidation with dinitrogen monoxide. Processes of this type are described in WO 2005/030690, WO 2008/000754 and WO 2010/086314, to which reference is hereby made in their entirety.

The dinitrogen monoxide can be used in pure form or in the form of a gas mixture which comprises dinitrogen monoxide. Within the context of the present invention, the term "gas mixture" refers to a mixture of two or more compounds which are in the gaseous state at ambient pressure and ambient temperature.

For the oxidation of the 1,5,9-cyclododecatriene-containing composition in step a), the dinitrogen monoxide or the dinitrogen monoxide-containing gas mixture can be used in gaseous form, in liquid form, in supercritical form or as a solution in a suitable solvent.

The oxidation of the 1,5,9-cyclododecatriene-containing composition in step a) can take place in the presence or absence of a catalyst.

In a specific embodiment, the dinitrogen monoxide is used in the form of a gas mixture which is produced as off-gas of another process, as described e.g. in WO 2006/032502, WO 2007/060160, WO 2008/071632, EP 08153953.8 and EP 08153952.0. It is also possible to use a mixture of different off-gases. Preferably, the dinitrogen monoxide is used in the form of a gas mixture which originates as off-gas from an adipic acid plant, a dodecanedioic acid plant, a hydroxylamine plant and/or a nitric acid plant. If desired, the gas mixture comprising dinitrogen monoxide can be subjected to a purification and/or concentration of the $N_2O$ content prior to its use for the oxidation. A suitable purification process comprises for example the absorption of the gas mixture in an organic solvent or water, the desorption of the gas mixture from the laden organic solvent or the laden water and the adjustment of the content of nitrogen oxides NOx in the gas mixture to at most 0.01 to 0.001% by volume, based on the total volume of the gas mixture. A process of this type is described for example in DE 10 2004 046 167.8, to which reference is hereby made in its entirety.

The oxidation of the 1,5,9-cyclododecatriene-containing composition with dinitrogen monoxide in step a) can take place without the addition of a solvent. If desired, the oxidation can also take place in the presence of a solvent which is inert under the reaction conditions. Here, essentially all customary solvents are suitable which have neither a C—C double bond nor a C—C triple bond nor an aldehyde group. These include e.g. cyclic alkanes, for example cyclododecane or cyclododecanone or saturated aliphatic or aromatic, optionally alkyl-substituted hydrocarbons.

The temperature during the oxidation with dinitrogen monoxide is preferably 140 to 350° C., particularly preferably 180 to 320° C.

The pressure during the oxidation with dinitrogen monoxide is preferably higher than the intrinsic pressure of the starting material and/or product mixture at the selected reaction temperature or the selected reaction temperatures. The pressure is preferably 1 to 1000 bar, particularly preferably 40 to 325 bar and in particular 50 to 200 bar.

For the oxidation with dinitrogen monoxide, the molar ratio of dinitrogen monoxide to 1,5,9-cyclododecatriene is generally in the range from 0.05 to 4, preferably in the range from 0.06 to 1, further preferably in the range from 0.07 to 0.5 and particularly preferably in the range from 0.1 to 0.4.

During the oxidation of the 1,5,9-cyclododecatriene-containing composition with dinitrogen monoxide in step a), an oxidation product is obtained which comprises the following components:
cyclododeca-4,8-dienone,
optionally unreacted 1,5,9-cyclododecatriene,
optionally at least one acyclic compound having 12 carbon atoms which has at least one aldehyde group.

The oxidation product obtained during the oxidation of the 1,5,9-cyclododecatriene-containing composition with dinitrogen monoxide in step a) can be subjected to a separation to give a fraction enriched in cyclododeca-4,8-dienone and a fraction depleted in cyclododeca-4,8-dienone. The separation can take place by customary processes known to the person skilled in the art, preferably distillatively. A process for the distillative separation of such an oxidation product is described in detail in WO 2010/086314, to which reference is made here in its entirety.

In general, during the preferred oxidation of cis,trans,trans-1,5,9-cyclododecatriene with dinitrogen monoxide, a cyclododeca-4,8-dienone isomer mixture results which comprises at least two of the isomers cis,trans-cyclododeca-4,8-dienone, trans,cis-cyclododeca-4,8-dienone and trans,trans-cyclododeca-4,8-dienone. Also possible, however, is the use of further isomer mixtures as are obtained e.g. by other oxidation processes.

Step b)

Preferably, the metathesis reaction in step b) is carried out at a temperature in the range from 0 to 200° C., particularly preferably from 10 to 150° C., in particular from 20 to 100° C.

The metathesis reaction can take place in the liquid phase or in the gas phase.

In a specific embodiment, for the metathesis reaction in step b), in addition to cyclododeca-4,8-dienone, at least one further compound capable of participating in the metathesis reaction is used.

The further compound is generally selected from cyclic compounds different from cyclododeca-4,8-dienone and having at least one C—C double bond. Preferably, the further compound has 1, 2 or 3 C—C double bonds.

The further compound can, if desired, have at least one functional group. Then, the carbon chain of the further compound is preferably interrupted by one or more non-adjacent groups selected from —O—, —S—, —NR$^a$—, —C(=O)—, —S(=O)— and/or —S(=O)$_2$—, where R$^a$ is preferably hydrogen, alkyl, cycloalkyl or aryl. In a specific embodiment, the carbon chain of the further compound is interrupted by one or more non-adjacent keto groups.

In addition to at least one C—C double bond, the further compound particularly preferably has no further functional group.

In one possible embodiment, the metathesis reaction in step b) is additionally carried out in the presence of at least one cycloalkamonoene or at least one cycloalkapolyene. The metathesis reaction is particularly preferably carried out in the presence of at least one cyclic oligobutadiene. In a specific embodiment, for the metathesis reaction in step b), in addition to cyclododeca-4,8-dienone, at least one further compound capable of participating in the metathesis reaction is used which is selected from 1,4-cyclooctadiene, 1,4,8-cyclododecatriene and mixtures thereof.

In a suitable embodiment, for the metathesis reaction in step b), a starting material is used which, in addition to cyclododeca-4,8-dienone, comprises at least one further compound capable of participating in the metathesis reaction in an amount of from 0.1 to 50% by weight, based on the total amount of cyclododeca-4,8-dienone and further compounds capable of participating in the metathesis reaction.

Specifically, for the metathesis reaction in step b), a starting material is used which comprises at least one cycloalkamonoene or at least one cycloalkapolyene in an amount of from 0.1 to 30% by weight, particularly preferably 0.5 to 25% by weight, in particular 1 to 20% by weight, based on the total amount of cyclododeca-4,8-dienone and cycloalkamonoene or cycloalkapolyene.

Also specifically, for the metathesis reaction in step b), a starting material is used which comprises 1,4-cyclooctadiene and/or 1,4,8-cyclododecatriene in an amount of from 0.1 to 30% by weight, particularly preferably 0.5 to 25% by weight, in particular 1 to 20% by weight, based on the total amount of cyclododeca-4,8-dienone and 1,4-cyclooctadiene and/or 1,4,8-cyclododecatriene.

By adding suitable compounds capable of participating in the metathesis reaction it is possible to control the composition of the product of the metathesis reaction. Thus, e.g. the use of suitable cyclic oligobutadienes, such as 1,4-cyclooctadiene and/or 1,4,8-cyclododecatriene, leads to a relatively high fraction of monoketones in the product of the metathesis reaction.

Preferably, the metathesis reaction in step b) is carried out in the presence of a solvent which is inert under the reaction conditions. Suitable solvents are, for example, aliphatic hydrocarbons, cycloaliphatic hydrocarbons, aromatic hydrocarbons, halogenated aliphatic hydrocarbons, esters of aliphatic and aromatic carboxylic acids with alkanols and mixtures thereof. These include e.g. n-pentane, n-hexane, n-heptane, n-octane, petroleum ether, ligroin, cyclopentane, cyclohexane, toluene, xylene, dichloromethane, chloroform, 1,2-dichloroethane, acetic ester and mixtures thereof.

It has been found that as the starting material concentration in the reaction mixture used for the metathesis increases, cyclic compounds with a relatively high number of carbon atoms are formed to an increasing degree. These are undesired for a use of the product of the metathesis reaction as fragrance or for providing a fragrance.

Preferably, for the metathesis reaction in step b), cyclododeca-4,8-dienone and, if present, cyclic compounds different therefrom having at least one C—C double bond are used in a total concentration in the range from 0.01 to 1 mol/l, particularly preferably in a total concentration in the range from 0.01 to 0.5 mol/l.

Suitable metathesis catalysts are in principle homogeneous and heterogeneous catalysts. Preferably, the metathesis catalyst used in step b) comprises at least one transition metal of groups 6, 7 or 8 of the Periodic Table of the Elements, particularly preferably Mo, W, Re or Ru.

Suitable homogeneous metathesis catalysts for use in step b) of the process according to the invention are e.g. salts or complexes of tungsten or of rhenium, e.g. WCl$_6$ or CH$_3$Re(CO)$_5$ or metal-carbene complexes which are preferably based on ruthenium or molybdenum. The catalysts based on Re, Mo or W are often used in combination with a co-catalyst, e.g. an organometallic complex of a main group element, such as aluminum alkyls, aluminum alkyl chlorides or zinc alkyls. The catalysts based on Re, Mo or W are also often used in combination with an activator, for example an oxygen-containing compound, such as ethanol or diethyl ether.

In a first preferred embodiment, in step b), a homogeneous catalyst is used which at least one ruthenium alkylidene complex, preferably a ruthenium alkylidene complex which additionally has at least one N-heterocyclic carbene as ligand.

Within the context of the present invention, the expression "alkyl" comprises straight-chain or branched alkyl. Alkyl preferably stands for C$_1$-C$_{20}$-alkyl, in particular C$_1$-C$_{12}$-alkyl and very particularly preferably C$_1$-C$_6$-alkyl. Examples of alkyl groups are in particular methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

Substituted alkyl groups can have one or more (e.g. 1, 2, 3, 4, 5 or more than 5) substituents depending on the length of the alkyl chain.

Alkyl radicals substituted by aryl ("arylalkyl" or "aralkyl") have at least one unsubstituted or substituted aryl group as defined below. Each aryl group has preferably 6 to 14, preferably 6 to 10, carbon atoms, and the alkyl moiety in aralkyl has preferably 1 to 20, preferably 1 to 12, carbon atoms. Arylalkyl stands for example for phenyl-C$_1$-C$_{10}$-alkyl, preferably for phenyl-C$_1$-C$_4$-alkyl, e.g. for benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)eth-1-yl, 1-(phenmethyl)-1-(methyl)eth-1-yl or 1-(phenmethyl)-1-(methyl)prop-1-yl; preferably for benzyl and 2-phenethyl.

Within the context of the invention, "cycloalkyl" refers to a cycloaliphatic radical having preferably 3 to 10, particularly preferably 5 to 8, carbon atoms. Examples of cycloalkyl groups are in particular cyclopropyl, cyclobutyl, cyclopentyl, cyclohexyl, cycloheptyl and cyclooctyl.

Within the context of the present invention, the expression "aryl" comprises mono- or polynuclear aromatic hydrocarbon radicals having usually 6 to 18, preferably 6 to 14, particularly preferably 6 to 10, carbon atoms. Examples of aryl are in particular phenyl, naphthyl, indenyl, fluorenyl, anthracenyl, phenanthrenyl, naphthacenyl, chrysenyl, pyrenyl, etc., and specifically phenyl or naphthyl.

Substituted aryls can have one or more (e.g. 1, 2, 3, 4, 5 or more than 5) substituents depending on the number and size of their ring systems. These are preferably selected independently of one another from alkyl, cycloalkyl and aryl. In this connection the alkyl, cycloalkyl and aryl substituents on the aryl can for their part be unsubstituted or substituted. Reference is made to the substituents specified above for these groups. One example of substituted aryl is substituted phenyl which generally carries 1, 2, 3, 4 or 5, preferably 1, 2 or 3, substituents.

Substituted aryl is preferably aryl substituted by at least one alkyl group ("alkylaryl"). Each alkyl group usually has 1 to 20, preferably 1 to 12, carbon atoms, and the aryl moiety in alkaryl has 6 to 14, preferably 6 to 10, carbon atoms. Alkylaryl groups can have one or more (e.g. 1, 2, 3, 4, 5, 6, 7, 8, 9 or more than 9) alkyl substituents depending on the size of the aromatic ring system. The alkyl substituents can be unsubstituted or substituted. In this regard, reference is made to the previous statements relating to unsubstituted and substituted alkyl. In a preferred embodiment, the alkylaryl groups have exclusively unsubstituted alkyl substituents. Alkylaryl is preferably phenyl which carries 1, 2, 3, 4 or 5, preferably 1, 2 or 3, particularly preferably 1 or 2, alkyl substituents having 1 to 12 carbon atoms.

Within the scope of the present invention, the expression "heteroaryl" (hetaryl) comprises heteroaromatic, mono- or polynuclear groups. In addition to the ring carbon atoms, these have 1, 2, 3, 4 or more than 4 ring heteroatoms. The heteroatoms are preferably selected from oxygen, nitrogen and sulfur. The hetaryl groups preferably have 5 to 18, e.g. 5, 6, 8, 9, 10, 11, 12, 13 or 14, ring atoms.

Within the context of the present invention, the expression "heterocycloalkyl" comprises non-aromatic, unsaturated or completely saturated, cycloaliphatic groups having in general 5 to 8 ring atoms, preferably 5 or 6 ring atoms. In the heterocycloalkyl groups, 1, 2, 3, 4 or more than 4 of the ring carbon atoms are replaced by heteroatoms or heteroatom-containing groups compared with the corresponding cycloalkyl groups. The heteroatoms or heteroatom-containing groups are preferably selected from —O—, —S—, —NR$^c$—, —C(=O)—, —S(=O)— and/or —S(=O)$_2$—. R$^c$ is preferably hydrogen, alkyl, cycloalkyl, heterocycloalkyl, aryl or hetaryl. Examples of heterocycloalkyl groups are in particular pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 1,2-oxazolin-5-yl, 1,3-oxazolin-2-yl and dioxanyl.

Preference is given to a process according to the invention, where the ruthenium-carbene complex is a compound of the formula (A),

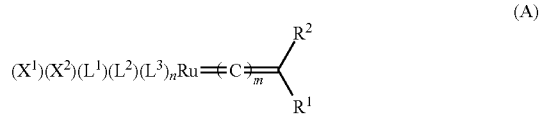

(A)

in which
X$^1$, X$^2$ can be identical or different and are in each case an anionic ligand,
L$^1$, L$^2$, L$^3$ can be identical or different and are in each case a neutral electron donor ligand,
R$^1$, R$^2$ can be identical or different and are in each case hydrogen or a C$_1$-C$_{40}$-carbon-containing radical,
  or two or more of the ligands or radicals selected from the group consisting of X$^1$, X$^2$, L$^1$, L$^2$, L$^3$, R$^1$ and R$^2$ are joined together and form a monocyclic or polycyclic ring system,
n is 0 or 1 and
m is 0, 1 or 2.

X$^1$, X$^2$ can be identical or different. In particular, X$^1$ and X$^2$ are identical. Preferably, X$^1$ and X$^2$, independently of one another, are selected from halogen, pseudohalogen, C$_1$-C$_6$-alkyl, C$_1$-C$_6$-alkyloxy, aryl or aryloxy. In particular, X$^1$ and X$^2$, independently of one another, are selected from fluorine, chlorine, bromine, iodine, cyano, thiocyano, methyl, ethyl, phenyl, phenyloxy, methyloxy or ethyloxy. Particularly preferably, X$^1$ and X$^2$ are both chlorine.

L$^1$, L$^2$, L$^3$ can be identical or different and are in each case a neutral electron donor ligand. Preferred neutral electron donor ligands are described in WO 2010/021740, page 16, paragraph 0070, and page 17, paragraph 0075, the cited document being incorporated in its entirety into the present disclosure. Particularly preferred neutral electron donor ligands are carbenes stabilized with two atoms of the 15th or 16th group of the Periodic Table of the Elements, in particular with two nitrogen atoms (so-called Arduengo carbenes), and also ethers, thioethers, amines or nitrogen-containing heterocycles, in particular pyridine or pyridine derivatives.

$R^1$, $R^2$ can be identical or different and are in each case hydrogen or a $C_1$-$C_{40}$-carbon-containing radical, such as, for example, $C_1$-$C_{20}$-alkyl, $C_2$-$C_{20}$-alkenyl, $C_2$-$C_{20}$-alkynyl, $C_6$-$C_{40}$-aryl, $C_7$-$C_{40}$-alkylaryl, $C_7$-$C_{40}$-arylalkyl, $C_5$-$C_{40}$-hetaryl, $C_5$-$C_{20}$-heterocycloalkyl or a silyl radical having 3 to 24 carbon atoms. Here, the carbon-containing radical can comprise further heteroatoms selected from the group of the elements consisting of F, Cl, Br, I, N, P, O and S and/or can be substituted with functional groups.

Two or more of the ligands or radicals selected from the group consisting of $X^1$, $X^2$, $L^1$, $L^2$, $L^3$, $R^1$ and $R^2$ can also be joined together to form a monocyclic or polycyclic ring system. Preferably, exactly one of the radicals $L^1$, $L^2$ or $L^3$ is joined with exactly one of the radicals $R^1$ or $R^2$, and these together form a monocyclic or polycyclic ring system.

Preferably, n is 0. Preferably, m is 0.

In a suitable embodiment, n is 0 and $L^1$ and $L^2$, independently of one another, are selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine and thioether. In particular, n is 0 and $L^1$ and $L^2$, independently of one another, are selected from pyridine or pyridine derivatives.

In the process according to the invention, particular preference is given to using a ruthenium-carbene complex of the formula (A) in which the neutral electron donor ligand $L^1$ is a carbene of the formula (B),

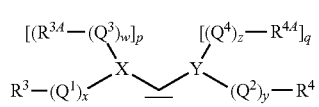

(B)

in which
X, Y can be identical or different, preferably identical, and are in each case a heteroatom selected from the group of the elements consisting of N, O, S and P, preferably N,
p is 0 if X is O or S, and p is 1 if X is N or P,
q is 0 if Y is O or S, and p is 1 if Y is N or P,
$Q^1$, $Q^2$, $Q^3$, $Q^4$, independently of one another, are in each case a divalent organic group having 1 to 40 carbon atoms, where additionally two or more substituents on adjacent atoms within $Q^1$, $Q^2$, $Q^3$ and/or $Q^4$ can be joined together in order to form an additional monocyclic or polycyclic structure,
w, x, y, z, independently of one another, are 0 or 1, and
$R^3$, $R^{3A}$, $R^4$, and $R^{4A}$ can be identical or different and, independently of one another, are in each case hydrogen or a $C_1$-$C_{40}$-carbon-containing radical.
$R^3$, $R^{3A}$; $R^4$, and $R^{4A}$ can be identical or different and are, independently of one another, in each case hydrogen or a $C_1$-$C_{40}$-carbon-containing radical, such as, for example $C_1$-$C_{20}$-alkyl, $C_2$-$C_{20}$-alkenyl, $C_2$-$C_{20}$-alkynyl, $C_5$-$C_{40}$-aryl, $C_7$-$C_{40}$-alkylaryl, $C_7$-$C_{40}$-arylalkyl, $C_2$-$C_{40}$-heteroaromatic radical, saturated $C_3$-$C_{20}$-heterocyclic radical or silyl radical having 3 to 24 carbon atoms, where the carbon-containing radical can comprise further heteroatoms selected from the group of the elements consisting of F, Cl, Br, I, N, P, O and S and/or can be substituted with functional groups.

In the carbenes of the formula (B), w, x, y and z are preferably all 0.

$Q^1$, $Q^2$, $Q^3$, $Q^4$ are preferably independently of one another a divalent hydrocarbon group, a substituted divalent hydrocarbon group, a divalent heteroatom-containing hydrocarbon group, a substituted and at the same time heteroatom-containing divalent hydrocarbon group or —(O)—.

In the process according to the invention, very particular preference is given to using a ruthenium-carbene complex of the formula (A) in which the neutral electron donor ligand $L^1$ is a carbene of the formula (B), in which m is 0, w, x, y, z are in each case 0, p, q are in each case 1, X, Y are N, and $R^{3A}$ and $R^{4A}$ are joined together and together form a divalent organic group Q having 1 to 40 carbon atoms.

A very particularly preferred ruthenium-carbene complex is the compound of the general formula (C)

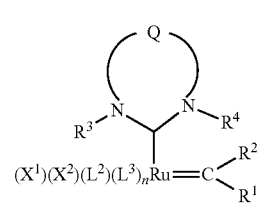

(C)

in which
$X^1$, $X^2$, $L^2$, $L^3$, $R^1$, $R^2$, $R^3$, $R^4$ and n have the meanings given above and
Q is a divalent organic group having 1 to 40 carbon atoms.

In the ruthenium-carbene complex of the formula (C), the neutral electron donor ligand $L^2$ is preferably phosphite, phosphinite, arsane, stibane, ether, amine, amide, imine, sulfoxide, carboxylate, nitrosyl, pyridine, substituted pyridine, imidazole, substituted imidazole, pyrazine, thioether or pyrrolidone.

Q is for example a divalent hydrocarbon group, a substituted divalent hydrocarbon group, a divalent heteroatom-containing hydrocarbon group or a substituted and simultaneously heteroatom-containing divalent hydrocarbon group.

In the ruthenium-carbene complex of the formula (C), any desired combinations of two or more of the groups $X^1$, $X^2$, $L^2$, $L^3$, $R^1R^2$, $R^3$ and $R^4$ can be joined together and form cyclic structures.

Ruthenium alkylidene complexes suitable as metathesis catalysts are also the "Grubbs" catalysts of the second generation, as are disclosed for example in R. H. Grubbs, Handbook of Metathesis, Vol. 1, p. 128, Wiley-VCH, 2003. These "Grubbs" catalysts of the second generation are catalysts which carry N-heterocyclic carbene ligands as well as or instead of the phosphane ligands. One example of a suitable "Grubbs" catalyst of the second generation is

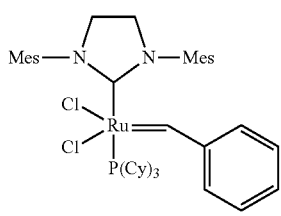

Cy=cyclohexyl,
Mes=2,4,6-trimethylphenyl.

Catalysts of this type are also described in U.S. Pat. No. 6,759,537, to which reference is made here in its entirety.

Ruthenium alkylidene complexes suitable as metathesis catalysts are also the "Hoveyda-Grubbs" catalysts

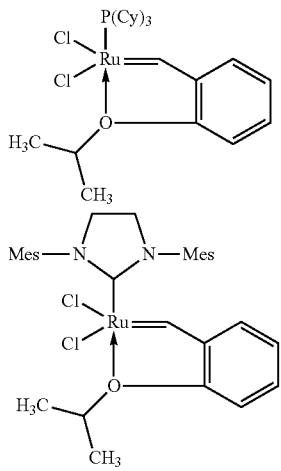

Catalysts of this type are also described in U.S. Pat. No. 6,921,735, to which reference is made here in its entirety.

Suitable metal complexes which have a carbene ligand and processes for their preparation are also described in WO 99/00396, to which reference is made here in its entirety.

Suitable ruthenium alkylidene complexes which have a N-heterocyclic carbene as ligand and processes for their preparation are also described in WO 99/51344, to which reference is made here in its entirety. There are for example compounds of the general formula (D)

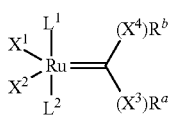
(D)

in which
$X^1$ and $X^2$ are identical or different and are an anionic ligand,
$X^3$ and $X^4$ are identical or different and are a chemical bond or are selected from —O—, —S—, —NR$^d$—, —C(=O)—, —S(=O)— and/or —S(=O)$_2$—, where R$^d$ is hydrogen, alkyl, cycloalkyl, heterocycloalkyl, aryl or hetaryl,
$R^a$ and $R^b$ are identical or different, where $R^a$ and $R^b$, together with the carbon atom to which they are bonded, can also form a cycle, and
$R^a$ and $R^b$, independently of one another, are hydrogen, in each case straight-chain or branched $C_1$-$C_{50}$-alkyl, $C_2$-$C_{50}$-alkenyl, $C_2$-$C_{50}$-alkynyl, $C_5$-$C_8$-cycloalkyl, $C_6$-$C_{30}$-aryl or silyl, where, in the $C_1$-$C_{50}$-alkyl, $C_2$-$C_{50}$-alkenyl, $C_2$-$C_{50}$-alkynyl, $C_5$-$C_8$-cycloalkyl, $C_6$-$C_{30}$-aryl or silyl radicals, one or more or all of the hydrogen atoms, independently of one another can be replaced by an alkyl, aryl, alkenyl, alkynyl, metallocenyl, halogen, nitro, nitroso, hydroxy, alkoxy, aryloxy, amino, amido, carboxyl, carbonyl, thio and/or sulfonyl group,
$L^1$ is a N-heterocyclic carbene of the general formulae E.1 to E.8 and $L^2$ is a neutral electron donor, in particular a N-heterocyclic carbene of the general formulae E.1 to E.4 or an amine, imine, phosphane, phosphite, stibine, arsine, carbonyl compound, carboxyl compound, nitrile, alcohol, ether, thiol or thioether,

(E.1)

(E.2)

(E.3)

(E.4)

(E.5)

(E.6)

(E.7)

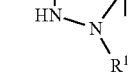

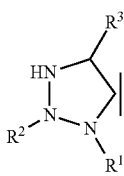
(E.8)

where $R^1$, $R^2$, $R^3$ and $R^4$ in the formulae E.1, E.2, E.3, E.4, E.5, E.6, E.7 and E.8 are identical or different from one another and $R^1$, $R^2$, $R^3$ and $R^4$, independently of one another, are hydrogen, in each case straight-chain or branched $C_1$-$C_{50}$-alkyl, $C_2$-$C_{50}$-alkenyl, $C_2$-$C_{50}$-alkynyl, $C_5$-$C_8$-cycloalkyl, $C_6$-$C_{30}$-aryl or silyl, where, in the $C_1$-$C_{50}$-alkyl, $C_2$-$C_{50}$-alkenyl, $C_2$-$C_{50}$-alkynyl, $C_5$-$C_8$-cycloalkyl, $C_6$-$C_{30}$-aryl or silyl radicals, one or more of the hydrogen atoms, independently of one another, can be replaced by an alkyl, aryl, alkenyl, alkynyl, metallocenyl, halogen, nitro, nitroso, hydroxy, alkoxy, aryloxy, amino, amido, carboxyl, carbonyl, thio and/or sulfonyl group, where at least one of the radicals $R^3$ and $R^4$ can also be a halogen, nitro, nitroso, alkoxy, aryloxy, amido, carboxyl, carbonyl, thio, silyl and/or sulfonyl group.

Suitable ruthenium alkylidene complexes, which have a N-heterocyclic carbene as ligand and processes for their preparation are also described in EP 1 022 282 A2, to which reference is made here in its entirety. These are compounds of the general formula (E)

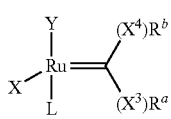
(E)

in which

X is an anionic ligand, $X^3$ and $X^4$ are identical or different and are a chemical bond or are selected from —O—, —S—, —NR$^d$—, —C(═O)—, —S(═O)— and/or —S(═O)$_2$—, where $R^d$ is hydrogen, alkyl, cycloalkyl, heterocycloalkyl, aryl or hetaryl, Y is a mono- to tridentate ligand which comprises a metal and is nonionically bonded to the ruthenium center, $R^a$ and $R^b$ are identical or different, where $R^a$ and $R^b$, together with the carbon atom to which they are bonded, can also form a cycle, and $R^a$ and $R^b$, independently of one another, are hydrogen, in each case straight-chain or branched $C_3$-$C_{50}$-alkyl, $C_2$-$C_{50}$-alkenyl, $C_2$-$C_{50}$-alkynyl, $C_5$-$C_8$-cycloalkyl, $C_6$-$C_{30}$-aryl or silyl, where, in the $C_1$-$C_{50}$-alkyl, $C_2$-$C_{50}$-alkenyl, $C_2$-$C_{50}$-alkynyl, $C_5$-$C_8$-cycloalkyl, $C_6$-$C_{30}$-aryl or silyl radicals, one or more or all of the hydrogen atoms, independently of one another, can be replaced by an alkyl, aryl, alkenyl, alkynyl, metallocenyl, halogen, nitro, nitroso, hydroxy, alkoxy, aryloxy, amino, amido, carboxyl, carbonyl, thio and/or sulfonyl group, L is a N-heterocyclic carbene of the general formulae E.1 to E.8,

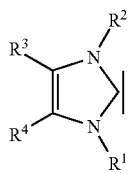
(E.1)

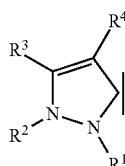
(E.2)

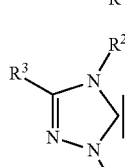
(E.3)

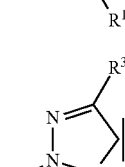
(E.4)

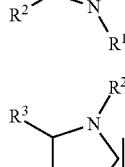
(E.5)

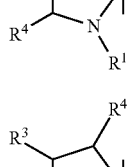
(E.6)

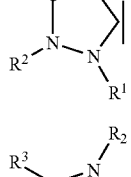
(E.7)

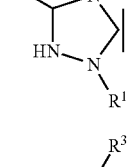
(E.8)

where $R^1$, $R^2$, $R^3$ and $R^4$ in the formulae E.1, E.2, E.3, E.4, E.5, E.6, E.7 and E.8 are identical or different from one another and $R^1$, $R^2$, $R^3$ and $R^4$, independently of one another, are hydrogen, in each case straight-chain or branched $C_1$-$C_{50}$-alkyl, $C_2$-$C_{50}$-alkenyl, $C_2$-$C_{50}$-alkynyl, $C_5$-$C_8$-cycloalkyl, $C_6$-$C_{30}$-aryl or silyl, where, in the $C_1$-$C_{50}$-alkyl, $C_2$-$C_{50}$-alkenyl, $C_2$-$C_{50}$-alkynyl, $C_5$-$C_8$-cycloalkyl, $C_6$-$C_{30}$-aryl or silyl radicals, one or more of the hydrogen atoms, independently of one another, can be replaced by an alkyl, aryl, alkenyl, alkynyl, metallocenyl, halogen, nitro, nitroso, hydroxy, alkoxy, aryloxy, amino, amido, carboxyl, carbonyl, thio and/or sulfonyl group, where at least one of the radicals $R^3$ and $R^4$ can also be a halogen, nitro, nitroso, alkoxy, aryloxy, amido, carboxyl, carbonyl, thio, silyl and/or sulfonyl group.

Suitable 5-fold coordinated metal complexes which have a carbene ligand and processes for their preparation are also described in WO 03/062253, to which reference is made here in its entirety. These are complexes which have a carbene ligand, a multidentate ligand and at least one ligand with considerable steric hindrance.

Suitable ruthenium alkylidene complexes and processes for their preparation are also described, e.g. in WO 2007/003135, to which reference is hereby made in its entirety.

Suitable ruthenium alkylidene complexes and processes for their preparation are also described e.g. in WO 2008/065187, to which reference is made here in its entirety.

WO 2009/097955, to which reference is made here in its entirety, describes photoactivatable, latent catalysts with the general formula

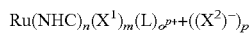

where
NHC is a N-heterocyclic carbene,
n=1 or 2;
$X^1$ is a $C_1$-$C_{18}$-mono- or polyhalogenated carboxylic acid or trifluoromethanesulfonate;
$X^2$ is a $C_1$-$C_{18}$-mono- or polyhalogenated carboxylic acid, trifluoromethanesulfonate, tetrafluoroborate, hexafluorophosphate or hexafluoroantimonate;
m=0, 1 or 2;
L is a $C_4$-$C_{18}$-carbonitrile or a $C_4$-$C_{18}$-carbodi- or -trinitrile;
o=6-n-m or 5-n-m and
p=2-m.

Ruthenium alkylidene complexes suitable as metathesis catalysts are also the so-called "Grubbs" catalysts of the first generation, e.g. of the formula

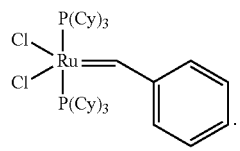

Cy = cyclohexyl

Catalysts of this type are also described in U.S. Pat. No. 5,969,170 and U.S. Pat. No. 6,111,121, to which reference is hereby made in their entirety.

Preferably, in step b), the catalyst used is at least one ruthenium alkylidene complex which is selected from dichloro(3-methyl-2-butenylidene)bis(tricyclopentylphosphine)ruthenium(II), isopentenylidene(1,3-dimesitylimidazolidin-2-ylidene)(tricyclohexylphosphine)ruthenium(II) dichloride, benzylidenebis(tricyclohexylphosphine)dichlororuthenium, 1,3-bis(2,4,6-trimethylphenyl)-2-(imidazolidinylidene)dichloro(phenylmethylene)(tricyclohexylphosphine)-ruthenium, dichloro(o-isopropoxyphenylmethylene)(tricyclohexylphosphine)-ruthenium(II), (1,3-bis(2,4,6-trimethylphenyl)-2-imidazolidinylidene)dichloro(o-isopropoxyphenylmethylene)ruthenium, 1,3-bis(2-methylphenyl)-2-imidazolidinylidene]-dichloro(phenylmethylene)(tricyclohexylphosphine)ruthenium(II), dichloro[1,3-bis(2-methylphenyl)-2-imidazolidinylidene](2-isopropoxyphenylmethylene)ruthenium(II), dichloro[1,3-bis(2,4,6-trimethylphenyl)-2-imidazolidinylidene][3-(2-pyridinyl)-propylidene]ruthenium(II), dichloro[1,3-bis(2,4,6-trimethylphenyl)-2-imidazolidinylidene]-(benzylidene)bis(3-bromopyridine)ruthenium(II), [1,3-bis(2,6-diisopropylphenyl)-4,5-dihydroimidazol-2-ylidene]-[2-isopropoxy-5-(trifluoroacetamido)phenyl]methyleneruthenium(II) dichloride, bis(tricyclohexylphosphine)-3-phenyl-1H-inden-1-ylidene-ruthenium(II) dichloride, bis(tricyclohexylphosphine)[(phenylthio)methylene]-ruthenium(II) dichloride, bis(tricyclohexylphosphine)[(phenylthio)methylene]-ruthenium(II) dichloride, 1,3-bis(2,4,6-trimethylphenyl)-4,5-dihydroimidazol-2-ylidene[2-(isopropoxy)-5-(N,N-dimethylaminosulfonyl)phenyl]methyleneruthenium(II) dichloride, 1,3-bis(2,4,6-trimethylphenyl)-4,5-dihydroimidazol-2-ylidene[2-(isopropoxy)-5-(N,N-dimethylaminosulfonyl)phenyl]methyleneruthenium(II) dichloride, [1,3-bis(2,4,6-trimethylphenyl)-2-imidazolidinylidene]-[2-[[(4-methylphenyl)imino]methyl]-4-nitrophenolyl][3-phenyl-1H-inden-1-ylidene]ruthenium(II) chloride; [1,3-bis(2,4,6-trimethylphenyl)-2-imidazolidinylidene][2-[[(2-methylphenyl)imino]methyl]phenolyl][3-phenyl-1H-inden-1-ylidene]ruthenium(II) chloride, 3-phenyl-1H-inden-1-ylidene-[bis(isobutylpropane)]ruthenium(II) dichloride, {[2-(isopropoxy)-5-(N,N-dimethylaminosulfonyl)phenyl]methylene}(tricyclohexylphosphin)ruthenium(II) dichloride, tricyclohexylphosphine[1,3-bis(2,4,6-trimethylphenyl)-4,5-dihydroimidazol-2-ylidene][(phenylthio)methylene]ruthenium(II) dichloride, tricyclohexylphosphine[1,3-bis(2,4,6-trimethylphenyl)imidazol-2-ylidene][3-phenyl-1H-inden-1-ylidene]ruthenium(II) dichloride, tricyclohexylphosphine[1,3-bis(2,4,6-trimethylphenypimidazol-2-ylidene][2-thienylmethylene]ruthenium(II) dichloride, tricyclohexylphosphine[2,4-dihydro-2,4,5-triphenyl-3H-1,2,4-triazol-3-ylidene][2-thienylmethylene]ruthenium(II) dichloride, tricyclohexylphosphine[4,5-dimethyl-1,3-bis(2,4,6-trimethylphenypimidazol-2-ylidene][2-thienylmethylene]ruthenium(II) dichloride, tricyclohexylphosphine[3-phenyl-1H-inden-1-ylidene][1,3-bis(2,4,6-trimethylphenyl)-4,5-dihydroimidazol-2-ylidene]ruthenium(II) dichloride, trifluoroacetato[4,5-dihydro-1,3-bis(2,4,6-trimethylphenyl)imidazol-2-ylidene]tetra(2,2-dimethylpropanenitrile)ruthenium(II) trifluoroacetate, tri(isopropoxy)-phosphine(3-phenyl-1H-inden-1-ylidene)[1,3-bis(2,4,6-trimethylphenyl)-4,5-dihydroimidazol-2-ylidene]ruthenium(II) dichloride or tricyclohexylphosphine[3-phenyl-1H-inden-1-ylidene[1,3-bis(2,4,6-trimethylphenyl)-4,5-dihydroimidazol-2-ylidene]-ruthenium(II) dichloride.

In a specific embodiment, in step b), the homogeneous catalyst used is at least one ruthenium alkylidene complex which is selected from complexes of the formula F, G or H

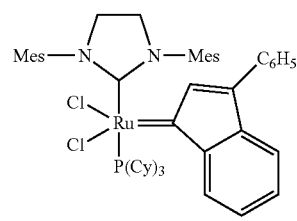

(F)

-continued

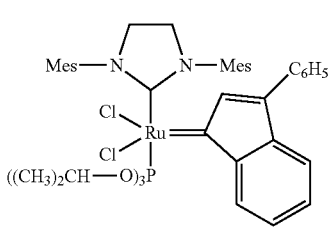

(G)

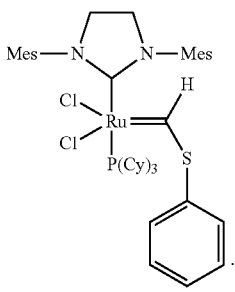

(H)

Cy = cyclohexyl
Mes = 2,4,6-trimethylphenyl

Catalysts which comprise an indenylidene-carbene (F) and their preparation are described in WO 2010/037550. Catalysts based on the phosphite-containing structures (G) are described in detail in WO 2011/117571. A detailed description of the compounds of the general formula (H) can be found in WO 99/00396. Reference is made here to the disclosure of these documents in their entirety.

In a second preferred embodiment, in step b), a heterogeneous catalyst is used which comprises a compound of tungsten or of ruthenium on an inorganic support material. Preferably, the compound of tungsten or of ruthenium is selected from $WO_3$, $Re_2O_7$ and $CH_3ReO_3$.

Step c)

The reaction mixture of the metathesis reaction obtained in step b) comprises the following components:
i) at least one cyclic compound having at least eight carbon atoms and at least one keto group,
ii) optionally at least one product of the metathesis reaction different from i), specifically cycloaliphatic olefins (unsaturated cyclic hydrocarbons)
iii) unreacted cyclododeca-4,8-dienone,
iv) optionally at least one unreacted cyclic or acyclic compound having at least one C—C double bond which is different from cyclododeca-4,8-dienone,
v) if present, the solvent used,
vi) the transition metal catalyst.

Preferably, the reaction mixture of the metathesis reaction obtained in step b) is subjected to a separation prior to its further use, specifically to its further use as fragrance or for providing a fragrance.

Preferably, the separation of the reaction mixture obtained in step b) comprises the separation of the transition metal catalyst used (component vi)). If a heterogeneous transition metal catalyst is used for the reaction in step b), then it is separated off e.g. by filtration or distillation. In the case of distillative separation of a heterogeneous transition metal catalyst, all volatile components are preferably separated off in an apparatus particularly for this purpose and known to the person skilled in the art. Preferably, distillative separation of a heterogeneous transition metal catalyst took place at elevated temperature and/or reduced pressure. If a homogeneous transition metal catalyst is used for the reaction in step b), then it is separated off e.g. by distillation, extraction, chromatography or a combination of at least two of these methods.

If a solvent is used for the metathesis reaction in step b), the separation of the reaction mixture obtained in step b) comprises preferably the separation of the solvent (component v)), preferably by distillation.

Separating off the catalyst (vi) used and, if present, separating off the solvent (v) used gives a reaction mixture which comprises the products of the metathesis reaction (component (i) and, if present, (ii)) the unreacted starting material (component (iii) and, if present, (iv)) and optionally also further undesired secondary components (impurities).

Preferably, the reaction mixture of the metathesis reaction comprises at least one cyclic compound which has at least 16 carbon atoms.

Preferably, the reaction mixture of the metathesis reaction comprises at least one cyclic compound selected from compounds having 12 or 16 or 20 or 24 carbon atoms.

Preferably, the reaction mixture of the metathesis reaction without transition metal catalyst and solvent consists to at least 5% by weight, preferably to at least 15% by weight, of at least one of the compounds I to IV

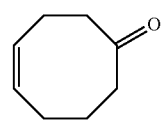

(I)

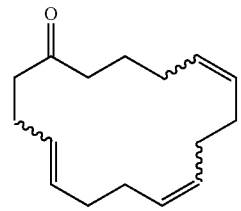 [SMILES: O=C1CCC=CCCC=CCCC=CCCC1]

(II)

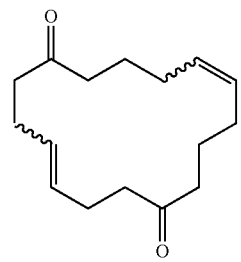

(III)

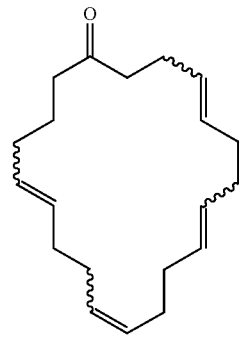

(IV)

Preferably, the reaction mixture of the metathesis reaction in step c) is subjected to a separation, giving at least one fraction which is enriched in at least one of the compounds I to IV, and at least one fraction which is depleted in at least one of the compounds I to IV

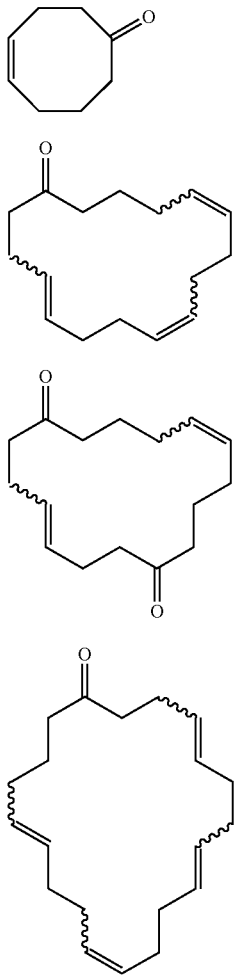

This separation preferably takes place after the catalyst (vi) used and, if present, the solvent (v) used has been separated off. It is also conceivable that when using a homogeneous catalyst, it is not separated off before the distillation, but remains in the bottom of the distillation.

Preferably, a reaction mixture which comprises at least one of the compounds I to IV as products of the metathesis reaction (i), if present further products of the metathesis reaction, unreacted starting materials (iii) and, if present, (iv) and optionally yet further undesired secondary components is subjected to a separation by customary methods known to the person skilled in the art. Preferably, the reaction mixture is subjected to distillative separation. Suitable apparatuses for distillative separation comprise distillation columns, such as tray columns, which can be provided with bubble caps, sieve plates, sieve trays, packings, packing bodies, valves, side offtakes, etc., evaporators, such as thin-film evaporators, falling-film evaporators, forced-circulation evaporators, Sambay evaporators, etc., and combinations thereof.

Preferably, the fraction depleted in at least one of the compounds I to IV is returned to the metathesis reaction in step b).

The compositions according to the invention and the compositions obtainable by the process according to the invention are particularly advantageous and suitable as fragrance or for providing a fragrance.

For the use as fragrance, the compositions according to the invention can be diluted as desired with at least one solvent customary in this field of application. By way of example, suitable solvents which may be mentioned are: ethanol, dipropylene glycol or ethers thereof, phthalates, propylene glycols, or carbonates of diols, preferably ethanol. Water is also suitable as a solvent for diluting the fragrance compositions according to the invention and can advantageously be used together with suitable emulsifiers.

A preferred embodiment of the fragrances according to the invention is characterized in that they comprise at least one compound which is selected from compounds of the formulae (I), (II), (III), (IV) or mixtures which comprise two, three or four of these compounds.

On account of the structural and chemical similarity of the components, the fragrances according to the invention have a high stability and shelf-life, and are characterized by a pleasant musk-like odor.

The fragrances according to the invention are suitable for the incorporation into cosmetic compositions and also utility items and consumer goods and/or compositions as described in more detail below. A further aspect of the present invention therefore relates to cosmetic compositions, consumer goods or utility items which comprise an organoleptically effective amount of the fragrances according to the invention, where the fragrances can be incorporated into the specified items or else applied thereto. In this connection, within the context of the entire present invention, an organoleptically effective amount is to be understood as meaning a particular amount which suffices, upon use as directed, to bring about a scent impression, specifically the impression of a pleasant musk odor, on the user or consumer.

Suitable cosmetic compositions are all customary cosmetic compositions. These are preferably perfume, Eau de Toilette, deodorants, soap, shower gel, bath gel, creams, lotions, sunscreens, compositions for the cleansing and care of the hair such as hair shampoo, rinse, hair gel, hair setting compositions in the form of liquids or foams and further cleansing or care compositions for the hair, compositions for decorative application to the human body, such as cosmetic sticks and pencils, e.g. lipsticks, lip care sticks, concealing sticks (concealers), blushers, eye shadow sticks, lip liner sticks, eyeliner sticks, eyebrow pencils, correction sticks, sunscreen sticks, anti acne sticks and comparable products, and also nail varnishes and other nail care products.

The fragrances according to the invention are suitable specifically for use in perfumes, e.g. as Eau de Toilette, shower gels, bath gels and body deodorants.

They are also suitable for aromatizing consumer goods or utility items into which they are incorporated and/or to which they are applied and imparting to them, as a result, a pleasant musk-like scent. Examples of consumer goods or utility items are: air fresheners (air care), cleaning compositions or care compositions for textiles (specifically detergents, fabric softeners), textile treatment compositions such as, for example, ironing aids, scouring compositions, cleaning compositions, care compositions for treating surfaces, for example furniture, floors, kitchen appliances, glass panes and windows, and also screens, bleaches, toilet blocks, lime scale removing compositions, fertilizers, building materials, mold removers, disinfectants, products for automobile and vehicle care and many more besides.

The metathesis products obtainable by the process according to the inventions or fractions or essentially pure compounds therefrom can also serve as valuable intermediates. They are suitable for further processing, e.g. by hydrogenation, Baeyer-Villiger oxidation to give macrocyclic lactones, synthesis building blocks of diverse specialty chemicals and fragrances, etc.

The examples below serve to illustrate the invention without limiting it in any way.

EXAMPLES

GC Analysis:
Instrument: HP 5890 Series II
Column: HP5 15 m×0.32 μm
Detector: FID detector
Injection: 0.5 μl
Temperature Program:
at 60° C. 5 min isotherm,
heat to 300° C. at 10° C./min,
15 min isotherm,
heat to 320° C. at 10° C./min,
18 min isotherm.

Example 1

The Ru catalyst of the formula (F) (4.7 mg, 4.9 μmol, 0.1 mol %) was added to a solution of cyclododeca-4,8-dienone (0.87 g, 4.9 mmol, 1 eq.) in toluene (100 ml) and the mixture was brought to 60° C.

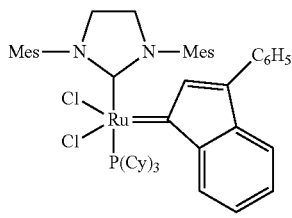
(F)

After 68 hours, the conversion of the dienone was 44%. The determination of the compounds I, II, III and IV were carried out by gas chromatography, as described above. The selectivities are given in table 1.

TABLE 1

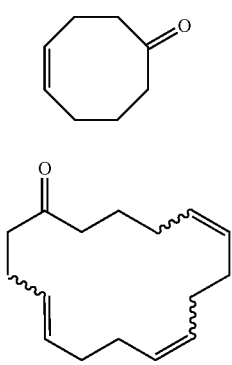

TABLE 1-continued

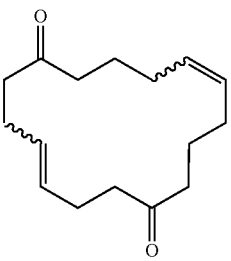 [SMILES: O=C1CCC=CCCC(=O)CCCC=CCCC1]
(III)

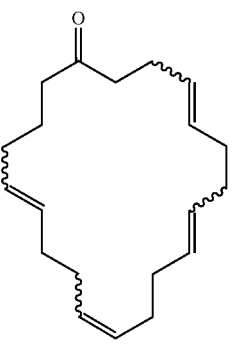 [SMILES: O=C1CCC=CCCC=CCCC=CCCC=CCCC1]
(IV)

| Compound | Mass selectivity, % |
|---|---|
| I | 3 |
| II | 5 |
| III | 2 |
| IV | 3 |
| $C_{20}$ diketones | 6 |

Example 2

Ru catalyst of the formula A (23.3 mg, 24.5 μmol, 0.1 mol %) is added to a solution of cyclododeca-4,8-dienone (4.35 g, 24.4 mmol, 1 eq.) in toluene (95 ml) and the mixture was brought to 60° C. After 68 h, the conversion of the dienone was 93%. The following selectivities were observed:

TABLE 2

| Compound | Mass selectivity, % |
|---|---|
| I | 1 |
| II | 2 |
| III | 2 |
| IV | 2 |
| $C_{20}$ diketones | 3 |

Note:
Mass selectivity may be defined as the ratio, given in %, of the mass of a product X located in the reaction discharge divided by the mass of the starting material used.

The invention claimed is:

1. A process for preparing at least one cyclic compound having at least eight carbon atoms and at least one keto group, wherein
   a) a cyclododeca-4,8-dienone-comprising starting material is provided, and
   b) the starting material is subjected to an olefin metathesis reaction in the presence of a transition metal catalyst.

2. The process of claim 1, wherein
   c) the olefin metathesis reaction takes place in a reaction mixture which is subjected to a separation.

3. The process of claim 1, wherein a 1,5,9-cyclododecatriene-containing composition is used for providing the cyclododeca-4,8-dienone-containing starting material in step a).

4. The process of claim 3, wherein the 1,5,9-cyclododecatriene-containing composition is subjected to an oxidation.

5. The process of claim 1, wherein the metathesis reaction in step b) is carried out at a temperature in the range from 0 to 200° C.

6. The process of claim 1, wherein the olefin metathesis reaction in step b) is carried out in the presence of a solvent that is inert under the reaction conditions.

7. The process of claim 1, wherein the olefin metathesis reaction in step b) is carried out in the presence of at least one additional cyclic compound having at least one C—C double bond, wherein the at least one additional cyclic compound is different from cyclododeca-4,8-dionone.

8. The process of claim 7, wherein the olefin metathesis reaction in step b) is carried out in the presence of at least one cyclic oligobutadiene.

9. The process of claim 1, wherein the cyclododeca-4,8-dionone- comprising starting material optionally comprises additional cyclic compounds having at least one C—C double bond different therefrom, and wherein the cyclododeca-4,8-dionone and the optional additional cyclic compounds are used for the metathesis reaction in step b) in a total concentration in the range from 0.01 to 1 mol/l.

10. The process of claim 1, wherein the transition metal catalyst used in step b) comprises at least one transition metal of group 6, 7 or 8 of the Periodic Table of the Elements.

11. The process of claim 1, wherein the transition metal catalyst used in step b) is a homogeneous catalyst which comprises at least one ruthenium alkylidene complex.

12. The process of claim 1, wherein the transition metal catalyst used in step b) is a homogeneous catalyst which comprises a compound of tungsten or of rhenium on an inorganic support material.

13. The process of claim 1, wherein the olefin metathesis reaction comprises at least 50% by weight, exclusive of the transition metal catalyst and solvent, of cyclic compounds having one or two keto groups.

14. The process of claim 1, wherein the olefin metathesis reaction takes place in a reaction mixture comprising at least one cyclic compound comprising at least 16 carbon atoms.

15. The process of claim 1, wherein the olefin metathesis reaction takes place in a reaction mixture comprising at least one cyclic compound selected from the group consisting of compounds having 12, 16, 20, and 24 carbon atoms.

16. The process of claim 2, wherein the separation gives at least one fraction enriched in at least one of the compounds I to IV:

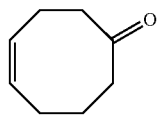
(I)

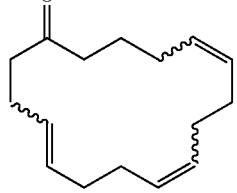
(II)

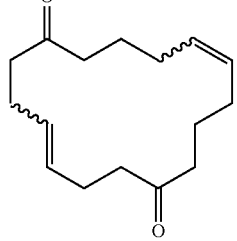
(III)

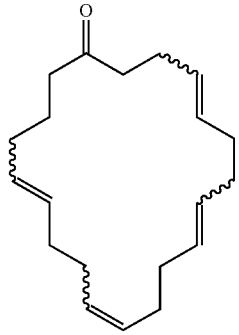
(IV)

and at least one fraction depleted in at least one of the compounds I to IV.

17. The process of claim 16, wherein the fraction depleted in at least one of the compounds I to IV is returned to the olefin metathesis reaction.

18. The process of claim 2, wherein the product from step b) or step c) is subjected to at least one further reaction.

19. A cosmetic composition, consumer good, or utility item which comprises an organoleptically effective amount of at least one cyclic compound having at least eight carbon atoms and at least one keto group as a fragrance, wherein the at least one cyclic compound is obtained by the process of claim 1.

* * * * *